United States Patent
Schliermann

(10) Patent No.: US 7,720,198 B2
(45) Date of Patent: May 18, 2010

(54) X-RAY FACILITY

(75) Inventor: Claus-Günter Schliermann, Kemnath (DE)

(73) Assignee: Siemens Aktiengesellschaft, Munich (DE)

( * ) Notice: Subject to any disclaimer, the term of this patent is extended or adjusted under 35 U.S.C. 154(b) by 23 days.

(21) Appl. No.: 11/661,305

(22) PCT Filed: Aug. 24, 2005

(86) PCT No.: PCT/EP2005/054149

§ 371 (c)(1),
(2), (4) Date: Feb. 23, 2007

(87) PCT Pub. No.: WO2006/024622

PCT Pub. Date: Mar. 9, 2006

(65) Prior Publication Data

US 2008/0101538 A1     May 1, 2008

(30) Foreign Application Priority Data

Sep. 3, 2004   (DE)   ........................ 10 2004 042 790

(51) Int. Cl.
*H05G 1/10* (2006.01)
(52) U.S. Cl. ........................................ 378/95; 378/108
(58) Field of Classification Search ................ 378/109, 378/111, 205–206, 95, 97, 108, 110, 112
See application file for complete search history.

(56) References Cited

U.S. PATENT DOCUMENTS

| | | | | |
|---|---|---|---|---|
| 4,896,343 | A  * | 1/1990 | Saunders | 378/95 |
| 6,272,368 | B1 | 8/2001 | Alexandrescu | |
| 6,501,820 | B2 | 12/2002 | Guendel | |
| 6,614,928 | B1 * | 9/2003 | Chung et al. | 382/154 |
| 2001/0019599 | A1 * | 9/2001 | Guendel | 378/15 |
| 2002/0188194 | A1 * | 12/2002 | Cosman | 600/426 |
| 2004/0081341 | A1 | 4/2004 | Cherek et al. | |
| 2005/0265516 | A1 * | 12/2005 | Haider | 378/20 |
| 2006/0079757 | A1 * | 4/2006 | Smith et al. | 600/416 |

FOREIGN PATENT DOCUMENTS

| | | |
|---|---|---|
| DE | 43 35 301 C1 | 12/1994 |
| DE | 197 43 500 A1 | 4/1999 |
| DE | 100 01 357 A1 | 8/2001 |
| DE | 102 32 676 A1 | 1/2004 |
| JP | 8-266536 | 10/1996 |

* cited by examiner

*Primary Examiner*—Hoon Song
(74) *Attorney, Agent, or Firm*—Brinks, Hofer, Gilson & Lione

(57) ABSTRACT

A controller for an X-ray device and an X-ray device with such a controller are provided. The X-ray device includes an X-ray generator, connected to the controller and at least one camera, connected to the controller. The controller is embodied to receive image data of a patient or object from the camera. The controller includes an analytical module, embodied to analyze image data from the camera and to generate at least one control signal for control of the X-ray generator depending on the result of the analysis of the image data, transmitted thereto by the controller.

20 Claims, 1 Drawing Sheet

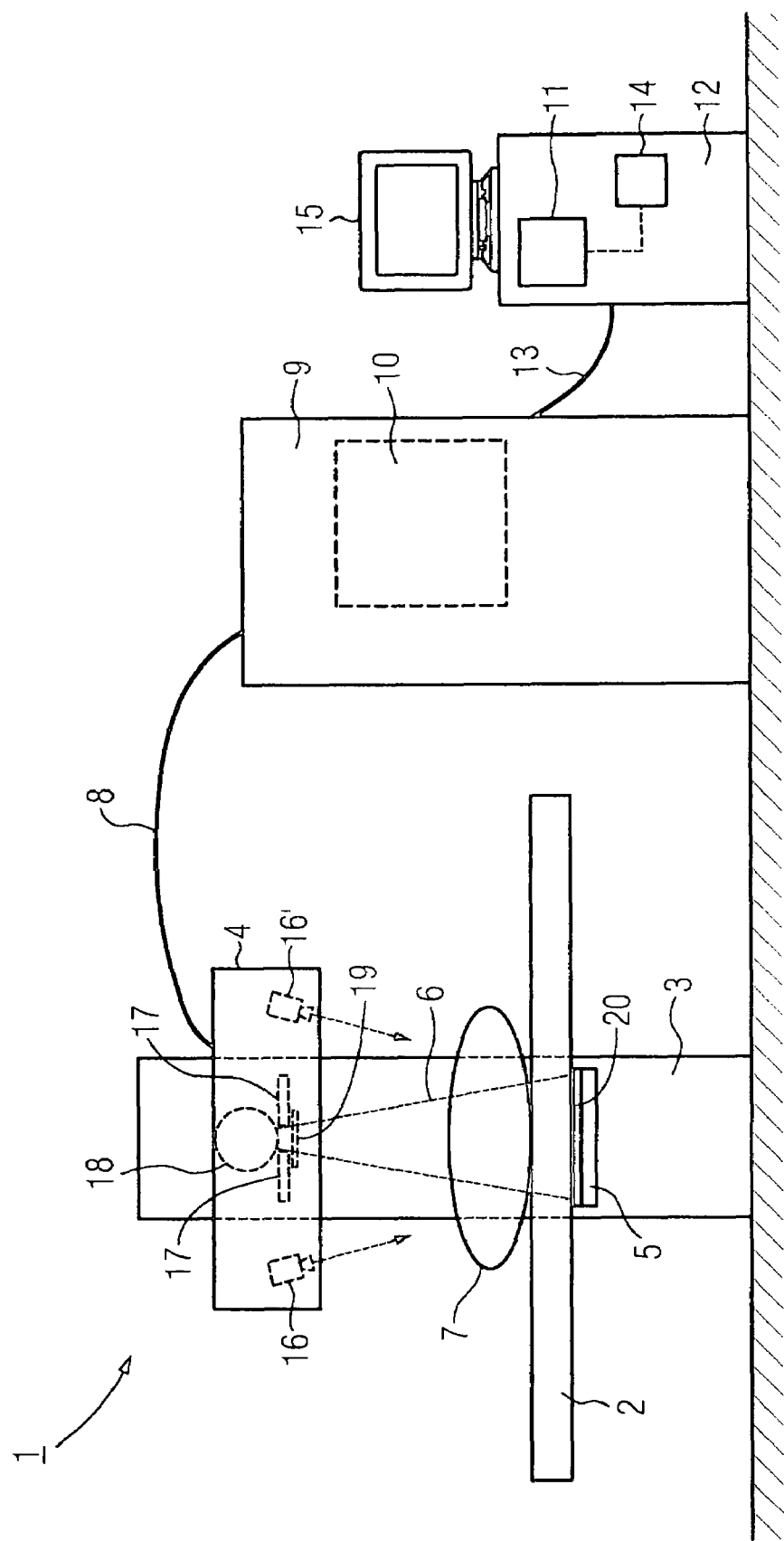

X-RAY FACILITY

The present patent document is a §371 nationalization of PCT Application Serial Number PCT/EP2005/054149, filed Aug. 24, 2005, designating the United States, which is hereby incorporated by reference. This patent document also claims the benefit of DE 10 2004 042 790.9, filed Sep. 3, 2004.

BACKGROUND

The present embodiments relate to an x-ray facility. Such an x-ray facility has a control facility, which includes a control interface for connection to at least one of the components of the x-ray facility to be controlled, and a camera interface for connection to at least one camera. To this end, the control facility is designed to receive image data of a patient or object from the camera interface.

X-ray facilities can be used for the diagnostic x-raying of patients or objects or the therapeutic x-raying of patients. Within the field of technology, x-ray facilities can be used, for example, for material examinations or for baggage control in airports. In the medical field, x-ray facilities are used for the therapeutic irradiation of tissues of the patient body, and for fluoroscopy purposes, which serve to generate x-ray images. The x-ray images are 2D projections of the x-rayed body parts. X-ray images of different 2D projections of the same body part can be used to generate 3D image data by way of imaging algorithms.

The characteristics of a 2D x-ray image, such as brightness, contrast or contrast intensity, essentially depend, in a technical sense, on the energy of the x-rays and on the x-ray dose. These characteristics are predefined by the x-ray generator, which activates the x-ray tubes and thus significantly influences the characteristics of the x-ray image. The characteristics of the x-ray image are influenced by the material x-rayed using the x-rays. The volume of the patients' body plays more of a decisive role during the diagnostic examination of said patient body than anything else. Parameters of the x-ray image detector, such as sensitivity, resolution, or scattered radiation grids, also play a decisive role.

In the field of x-ray diagnostics, different patient-dependent adjustments must be carried out by an operator of the x-ray facility prior to generating an x-ray recording. Many of these adjustments can be derived from the size and volume of the patient. For instance, the parameters of the x-ray generator must be adjusted to the volume of the body. Adjustments are also to be carried out based on the location of the patient. For instance, the position of the x-ray detector must be adjusted to the location of the organ or body part to be examined. The diaphragm of the x-ray emitter is adjusted as a function of the size of the organ or body part to be examined, in order to limit the x-ray beam bundle to the smallest possible size and thus to keep the radiation exposure for the patient as minimal as possible.

The operator carries out the geometric adjustments, for example, orientation and diaphragm adaptation, by hand using an optical light visor. The operator estimates the patient volume and adjusts the recording parameters of the x-ray generator. Alternatively, an automatic exposure system can be provided. The automatic exposure system requires an additional dose/measuring device that is upstream of the x-ray image detector.

JP 08-266536 discloses an x-ray facility, which includes at least one moveable component. The moveable component can be, for example, an x-ray image detector. The moveable component should be able to be moved as fast as possible and should be protected against collisions with obstacles. Distance sensors that operate in a touch-free manner are attached to the moveable component. The distance sensors are be able to detect whether a minimal distance from obstacles has not been met.

DE 197 43 500 A1 discloses an x-ray facility, with which the collision of moveable components with obstacles or even the patient to be examined is likewise to be avoided. The x-ray facility includes a light emitter for emitting a light fan and a camera for detecting the patient and/or the obstacle. 3D data is generated with the aid of the camera. The 3D data can be used to avoid collisions. The light emitters and cameras may operate in the infrared wavelength range.

DE 102 32 676 A1 discloses the positioning of a patient to be examined in a computed tomograph. An image recording device records the image data of the patient to be examined. The image data is subject to an image processing, which automatically proposes a body region for the examination. The patient can be automatically positioned such that the body region to be examined is located in the scanning area of the computed tomograph.

SUMMARY

The present embodiments may obviate one or more of the drawbacks or limitations inherent in the related art. For example, in one embodiment, an x-ray facility includes a more effective automation of the controller and an increased protection against defective adjustments by operators.

In one embodiment, an x-ray facility includes a control facility. The control facility includes a control interface for connection to at least one of the components of the x-ray facility to be controlled. The control facility includes a camera interface for connection to at least one camera. The control facility can be designed to receive image data of a patient or object from the camera interface. The control facility includes an evaluation module, which is designed to evaluate image data received from the camera interface and to generate at least one control signal as a function of a result of the evaluation of the image data. The at least one control signal controls at least one component provided for the diagnostic or therapeutic x-raying of the patient or object. The control signal is made available by way of the control interface.

The components to be controlled directly significantly influence the characteristics of the x-ray radiation when passing through the body or object, such as for instance an x-ray generator, a diaphragm or a filter, or such components, which decisively influence the characteristics of an x-ray image to be generated, such as for instance in addition to the said x-ray detector or scattered radiation grid.

The x-ray facility can be adjusted on the basis of an automatic evaluation of image data of the patient or object with respect to the characteristics of an x-ray image. The adjustment of the x-ray facility is otherwise estimated by an operator on the basis of an optical impression, or, in some circumstances, by a visual judgment. The automatic evaluation of image data aids the operator with his/her work since there is no need for either the optical measures or the following manual parameter inputs The susceptibility to false estimations or false entries by the operator is also reduced. The parameter selection does not depend on the experience or skill of the operator.

In one embodiment, the camera interface is designed such that a CCD camera, a laser scanner, or an infrared camera can be connected. Current cameras can be connected by way of the camera interface. The cameras operating on the basis of well-known principles. It is possible to revert back to a broad base of experience in order to evaluate image data. The use of a CCD camera obtains image data, which can also be examined optically by an operator or a doctor. The operator or doctor can generate additional information based on the image data for the control of the x-ray facility or the diagnosis of the patient or object. The use of a laser scanner allows methods for 3D image data acquisition to be used. The use of an infrared camera allows a measurement using a particularly simple camera structure by foregoing visible light and distance information to be easily obtained.

In one embodiment, the evaluation module can be designed such that it evaluates 2D image data received from the camera interface. The evaluation includes the determination of the 2D contour of the patient or object. The determination of 2D image data can be realized in a particularly simple manner. The correct position of the patient or object can be monitored from a determined 2D contour. Conclusions can be drawn about the volume of the object from the evaluation of the 2D image data with respect to typical variables, for example, a waist width or a joint diameter. The conclusions can be used again to control parameters such as x-ray voltage or x-ray current time product.

In one embodiment, the evaluation module is designed to evaluate 3D image data received from the camera interface. The evaluation includes the determination of the volume of the patient or object. The volume of the patient or object can be directly determined and the size of the volume to be x-rayed can be accurately determined. On the basis of these variables, parameters such as x-ray voltage or x-ray current time product can be adjusted to an optimal value for the x-ray therapy or x-ray diagnosis.

In one embodiment, the evaluation module is designed to evaluate 3D image data received from the camera interface. The evaluation includes the determination of a distance from the patient or object. A minimum distance from the patient or object can be monitored. Geometric variables, for example, the aperture, of the x-ray path between the x-ray tube and the x-ray image detector can be automatically controlled.

In one embodiment, an x-ray facility includes a control facility and an x-ray generator. The x-ray generator is connected to the control facility and has at least one camera. The at least one camera is connected to the control facility. The control facility can be designed to receive image data of a patient or object from the camera. The control facility includes an evaluation module. The evaluation module is set up to evaluate image data received from the camera and to generate at least one control signal for controlling the x-ray generator as a function of a result of the evaluation of the image data. The control signal is transmitted to the evaluation module by the control facility.

An optimal adjustment of the parameters of the x-ray generator is enabled for the x-ray therapy or x-ray diagnosis on the basis of an automatic evaluation of image data of the patient or object. The adjustable parameters of the x-ray generator include, for example, the x-ray voltage and the x-ray current time product, which are substantially material to the effect of the x-ray radiation. During the x-ray diagnosis, these parameters significantly influence the quality of the x-ray images to be generated.

In one embodiment, the evaluation module is designed to evaluate 3D image data received from the camera interface. The evaluation includes the determination of the volume of the patient or object. The volume of the patient or object can be determined directly and thus the volume to be x-rayed is known precisely. The precise knowledge of the volume to be x-rayed enables the parameters of the x-ray generator to be optimally adjusted for the x-ray diagnosis or x-ray therapy.

In one embodiment, the control signal is designed to control the x-ray voltage of the x-ray generator. An adaptation of the generator voltage for improving the image quality is carried out on the basis of the automatic evaluation of the image data. The adaptation of the generator voltage simultaneously allows for a reduction in the exposure using soft x-rays, for example, x-rays with lower energy, which do not have a positive effect in terms of image quality. The x-ray voltage is reduced for thinner patients or objects. The x-ray voltage is increased for larger volume patients or objects. While the adaptation of the x-ray voltage is not implicitly necessary in order to generate a correctly exposed x-ray image, it nevertheless significantly influences the x-ray exposure and the contrast intensity of the x-ray image to be generated.

In one embodiment, the control signal is designed to control the current time product of an x-ray generator. The x-ray current time product can be adjusted to the volume of the patient or object, in order to achieve a correct exposure of the x-ray image to be generated. This contributes to improving the image quality, particularly with x-ray facilities without automatic exposure systems, by which the x-ray current time product is controlled automatically. The x-ray current time product is increased with larger volume patients or objects and is reduced with thinner patients or objects.

BRIEF DESCRIPTION OF THE DRAWING

FIG. 1 is schematic representation of an x-ray facility having automated image data evaluation.

DETAILED DESCRIPTION

In one embodiment, as shown in FIG. 1, an x-ray facility 1 includes automated image data evaluation.

A patient 7 to be examined is positioned on a patient support table 2. An x-ray image detector 5 is arranged below the patient support table 2. The x-ray image detector 5 can generate x-ray image data on the basis of incidental x-rays. A film screen system and also a digital detector (flat screen detector, FD) can be used as an x-ray image detector 5. Image amplifiers can also be used as an x-ray image detector 5.

The patient support table 2 is attached to a stand 3, on which it can be moved, together with the x-ray image detector 5, in the vertical and horizontal direction. An x-ray emitter 4 is attached to the stand 3. The x-ray emitter 4 is moveable in the vertical and horizontal direction. An x-ray tube 18 is an integral part of the x-ray emitter 4. The x-ray tube 18 generates an x-ray beam bundle 6. The x-ray emitter 4 and patient support table 3 can be aligned such that the x-ray beam bundle 6, shown with a dashed line in the figure, passes through the patient 7 and subsequently hits the x-ray image detector 5.

The geometry of the x-ray beam bundle 6 in the region of the body volume of the patient 7 to be x-rayed depends on the distance and alignment of the x-ray emitter 4 from the patient support table 2. The geometry of the x-ray bundle 6 can be influenced by a diaphragm 17, which can narrow the x-ray beam bundle 6 using aperture plates in two horizontal directions. The contour of the x-ray beam bundle 6 can be adjusted to the contour of the body volume to be x-rayed in each instance.

The characteristics of the x-rays can also be influenced by a filter 19. The filter 19 can optimize the frequency spectrum of the x-rays. The filter 19 can operate on the basis of refraction, with the control then being carried out by way of the inclination of the filter 19 and thus by way of the Bragg angle of the x-ray refraction. The filter 19 can also operate on the basis of different filter materials having different optical indices, with the control then being carried out by inserting and/or changing different filters 19.

The characteristics of the x-ray images, which are generated by the x-ray image detector 5, are influenced by a scattered radiation grid 20. The scattered radiation grid 20 blocks x-rays, which would hit the x-ray image detector 5 after scattering processes in the patient 7. X-rays not emanating from the x-ray tube 18 but hitting the x-ray image detector 5 are blocked by the grid. To avoid unwanted mapping of the grid in the x-ray image, the grid is moved during the x-ray process. The manner and movement of the scattered radiation grid 20 can be controlled in order to optimize the x-ray images to be generated.

The x-ray emitter 4 is connected to a system cabinet 9 by way of a supply line 8. The system cabinet 9 includes, for example, an x-ray generator 10. The x-ray generator 10 generates the x-ray voltage, with which the x-ray tube 18 is operated. The x-ray generator 10 specifies the x-ray voltage and thus the energy of the x-rays of the x-ray tube 18 and the application duration. The x-ray voltage significantly influences the x-ray current. In conjunction with the x-ray tube 18, the x-ray generator 10 determines the parameters of the x-ray beam which are significant to the x-ray fluoroscopy of the patient 7.

The system cabinet 9 is connected to an operating console 12 by a control line 13. The operating console 12 includes a display device 15, which can display a user interface for an operator. An integral part of the operating console 12 is a control facility 11. The control facility 11 can be operated by an operator. The control facility 11 controls the x-ray generator 10. The control facility 11 can control further system components, for example, the position of the diaphragm 17 and the position and location of the x-ray emitter 4 and of the patient support table 2.

The x-ray emitter 4 includes two cameras 16, 16'. The two cameras 16, 16' record image data of the patient 7 on the basis of optically visible or infrared light. The cameras 16, 16' are not suited to record x-ray images because they operate in a wavelength range which involves the lowest possible, even non-existent radiation exposure for the patient 7. Image data from the cameras 16, 16' likewise passes across the supply line 8 and the control line 13 to the control facility 11.

The control facility 11 receives this image data and feeds it to an evaluation module 14. The evaluation module 14 carries out an automatic evaluation of the image data. Typical variables, for example, a contour of the patient 7, the diameter of body parts, or the body length, can be determined from 2D image data. Typical variables of this type allow conclusions to be drawn about the volume of the patient. These conclusions influence the size of the body volume to pass through the radiation bundle 6 and thus the characteristics of the x-rays hitting the x-ray image detector 5. If the cameras 16, 16' provide 3D image data, or if 3D image data can be determined by a suitable, for example, steriotactic, arrangement of the cameras 16, 16', the evaluation module 14 also evaluates the 3D image data and has instantaneous and direct information relating to the volume of the patient 7 at its disposal.

The evaluation module 14 can generate a signal on the basis of the patient's volume determined indirectly or directly. The signal is dependent on the patient's volume and is sent to the control facility 11. A tabular assignment of volume values and signals dependent on the patient's volume can be accessed. The dependent signal can be derived from a calculation of a formula with the volume value as a variable. The control facility 11 can generate a control signal as a function of the patient's volume. The control signal being used to control the x-ray generator 10 as a direct or indirect function of the volume of the patient 7 and thus of the size of the body volume to be x-rayed. The x-ray voltage or the x-ray current time product can be, for example, reduced with thinner patients or increased with larger volume patients.

It is possible to control the diaphragm 17 as a function of the volume, in order to predetermine the geometry of the x-ray beam bundle 6 in the region of the patient 7 to be x-rayed. The filter 19 can also be automatically controlled as a function of an evaluation by the evaluation module 14, and the scattered radiation grid 20.

In one exemplary embodiment, two cameras 16, 16' are used. The use of two cameras enables 2D image data to be detected, from which 3D image data can be generated using a corresponding image processing algorithm.

The invention is not restricted to embodiment variants having two or more cameras, but can instead also be realized using only one camera. The use of a single camera on a static mounting allows solely 2D image data to be detected. The generation of 3D image data is not possible. Significant variables can be determined on the basis of 2D image data, depending on which variables the x-ray control parameters can be automatically adjusted. For example, a 2D projection of the patient can be used to determine the patient or object diameter in this projection. The volume can be estimated from, for example, the diameter. A parameter adjustment for the x-ray control can be determined using the volume estimated in this manner.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. An x-ray system comprising:
    a control facility that includes a control interface connected to at least one component of the x-ray facility to be controlled; and
    a camera interface connected to at least one camera attached to an x-ray emitter of the x-ray facility, the control facility being operable to receive image data of a patient from the camera interface,
    wherein the control facility includes an evaluation module, the evaluation module being operable to evaluate image data received from the camera interface to determine a volume of the patient and to generate at least one control signal as a function of the volume, the control signal controlling at least one component provided for a diagnostic or therapeutic x-raying of the patient as a function of the volume of the patient, and
    wherein the signal is made available by the control interface.

2. The x-ray system as claimed in claim 1, wherein the control interface is connected with and operative to control a diaphragm, a filter, a scattered radiation grid, an x-ray detector, or any combination thereof.

3. The x-ray system as claimed in claim 1, wherein the camera interface is connected to a CCD camera, a laser scanner, or an infrared camera.

4. The x-ray system as claimed in claim 1, wherein the evaluation module is operable to evaluate 2D image data received from the camera interface, the evaluation comprising the determination of a 2D contour of the patient.

5. The x-ray system as claimed in claim 4, wherein the evaluation comprises the determination of the position of the patient.

6. The x-ray system as claimed in claim 4, wherein the volume of the patient is estimated using a diameter of the 2D contour.

7. The x-ray system as claimed in claim 1, wherein the evaluation module is operable to evaluate 3D image data received from the camera interface.

8. The x-ray system as claimed in claim 7, wherein the evaluation comprises the determination of a 3D envelope surface of the patient.

9. The x-ray system as claimed in claim 1, wherein the evaluation comprises the determination of a distance from the patient to the at least one camera.

10. The x-ray system as claimed in claim 1, wherein the control signal is operable to control an x-ray voltage of an x-ray generator.

11. The x-ray system as claimed in claim 1, wherein the control signal is operable to control a current time product of an x-ray generator.

12. The x-ray system as claimed in claim 11, wherein the current time product is controlled as a function of the volume of the patient, such that x-ray exposure is reduced for smaller volume patients and increased for larger volume patients.

13. The x-ray system as claimed in claim 1, wherein the control interface is connected with and operative to control a diaphragm as a function of the volume, such that a geometry of an x-ray beam in the region of the patient corresponds to the volume of the patient.

14. The x-ray system as claimed in claim 1, wherein the control signal controls the at least one component as a function of the size of the volume of the patient.

15. An x-ray facility comprising:
a control facility connected with an x-ray generator, and
at least one camera directly attached to an x-ray emitter of the x-ray facility, the at least one camera connected to the control facility, the control facility being operable to receive image data of a patient from the at least one camera,
wherein the control facility comprises an evaluation module operable to evaluate image data received from the at least one camera, determine a volume of the patient and generate at least one control signal to control the x-ray generator based on the volume of the patient, the control signal being transmitted to the x-ray generator by the control facility.

16. The x-ray facility as claimed in claim 15, wherein the camera interface is connected to a CCD camera, a laser scanner, or an infrared camera.

17. The x-ray facility as claimed in claim 15, wherein the evaluation module is operable to evaluate 2D image data received from the camera interface, the evaluation comprising the determination of a 2D contour of the patient.

18. The x-ray facility as claimed in claim 15, wherein the evaluation module is operable to evaluate 3D image data received from the camera interface, the evaluation comprising the determination of a volume of the patient.

19. The x-ray facility as claimed in claim 15, wherein the control signal is operable to control a x-ray voltage of the x-ray generator.

20. The x-ray facility as claimed in claim 15, wherein the control signal is operable to control a current time product of an x-ray generator.

* * * * *